(12) United States Patent
Beraud et al.

(10) Patent No.: US 6,387,679 B1
(45) Date of Patent: May 14, 2002

(54) MOTOR PROTEINS AND METHOD FOR THEIR USE

(75) Inventors: Christophe Beraud, San Francisco; Richard Freedman, San Mateo, both of CA (US)

(73) Assignee: Cytokinetics, Inc., South San Francisco, CA (US)

(*) Notice: Subject to any disclaimer, the term of this patent is extended or adjusted under 35 U.S.C. 154(b) by 0 days.

(21) Appl. No.: 09/723,429

(22) Filed: Nov. 27, 2000

Related U.S. Application Data

(63) Continuation of application No. 09/634,957, filed on Aug. 8, 2000.

(51) Int. Cl.[7] .......................... C12N 9/16; C12N 15/00; C12N 5/00; C07K 1/00; C07H 21/04

(52) U.S. Cl. ....................... 435/196; 530/350; 435/325; 435/252.3; 435/320.1; 536/23.2

(58) Field of Search ............................... 435/196, 320.1, 435/325, 252.3; 530/350; 536/23.2

(56) References Cited

PUBLICATIONS

Database GenEmbl, Accession No. AJ132889, Jul. 1999.*

\* cited by examiner

*Primary Examiner*—Rebecca E. Prouty
*Assistant Examiner*—Maryam Monshipouri
(74) *Attorney, Agent, or Firm*—Lauren L. Stevens, Esq.; Beyer Weaver & Thomas LLP

(57) ABSTRACT

The invention provides isolated nucleic acid and amino acid sequences of HsKif9, antibodies to HsKif9, methods of screening for HsKif9 modulators using biologically active HsKif9, and kits for screening for HsKif9 modulators.

13 Claims, 6 Drawing Sheets

FIG. 1 (Part 1)

```
AATGGGTACT AGGAAAAAAG TTCATGCATT TGTCCGTGTC AAACCCACCG
ATGACTTTGC TCATGAAATG ATCAGATACG GAGATGACAA AAGAAGCATT
GATATTCACT TAAAAAAAGA CATTCGGAGA GGAGTTGTCA ATAACCAACA
GACAGACTGG TCGTTTAAGT TGGATGGAGT TCTTCACGAT GCCTCCCAGG
ACTTGGTTTA TGAGACAGTT GCAAAGGATG TGGTTTCTCA GGCCCTCGAT
GGCTATAATG GCACCATCAT GTGTTATGGG CAGACGGGAG CTGGCAAGAC
ATACACCATG ATGGGGGCAA CTGAGAATTA CAAGCACCGG GGGATCCTCC
CTCGTGCCCT GCAGCAGGTT TTTAGGATGA TCGAAGAACG CCCCACACAT
GCCATCACTG TGCGTGTTTC CTACTTGGAA ATCTATAATG AGAGCCTGTT
TGATCTCCTG TCCACTCTGC CCTATGTTGG ACCCTCAGTC ACACCAATGA
CCATCGTGGA AAACCCTCAA GGAGTCTTCA TTAAGGGCTT GTCAGTTCAC
CTCACAAGTC AGGAGGAGGA TGCATTCAGC CTCCTTTTTG AGGGTGAGAC
CAACAGGATT ATAGCCTCCC ACACTATGAA CAAAAACTCT TCCAGATCAC
ACTGCATTTT CACCATCTAC TTAGAGGCCC ATTCCCGGAC CTTATCAGAG
GAAAAGTACA TCACTTCCAA AATTAACTTG GTGGATCTGG CAGGCTCAGA
GAGGCTGGGG AAGTCTGGGT CTGAGGGCCA AGTCCTGAAG GAAGCCACCT
ACATCAACAA ATCGCTCTCA TTCCTGGAGC AGGCCATCAT TGCCCTTGGG
GACCAGAAGC GGGACCACAT CCCCTTTCGG CAGTGCAAGC TCACCCACGC
TCTGAAGGAC TCGTTAGGGG GAAACTGCAA TATGGTCCTC GTGACAAACA
TCTATGGAGA AGCTGCCCAG TTAGAAGAAA CGCTATCTTC ACTGAGATTT
GCCAGCAGGA TGAAGCTAGT CACCACTGAG CCTGCCATCA ATGAAAAGTA
TGATGCTGAG AGAATGGTCA AGAACCTGGA GAAGGAACTA GCACTACTCA
AGCAGGAGCT GGCTATCCAT GACAGCCTGA CCAACCGCAC CTTTGTGACC
TATGACCCCA TGGATGAAAT CCAGATTGCT GAGATCAACT CCCAGGTGCG
GAGGTACCTG GAGGGACAC TGGACGAGAT CGACATAATC AGCCTTAGAC
AGATCAAGGA GGTGTTCAAC CAGTTCCGGG TGGTTCTGAG CCAACAGGAA
CAGGAAGTGG AGTCCACTTT GCGCAGGAAG TACACCCTCA TTGACAGGAA
TGACTTTGCA GCCATTTCTG CTATCCAGAA GGCGGGGCTT GTGGATGTTG
ATGGCCACCT AGTGGGTGAG CCTGAAGGAC AAAACTTTGG ACTCGGAGTC
```

FIG. 1 (Part 2)

```
GCCCCTTTCT CTACCAAACC TGGGAAGAAA GCCAAGTCCA AGAAGACATT
CAAAGAGCCA CTCAGCTCCT TGGCAAGAAA GGAAGGTGCC AGCAGCCCTG
TGAATGGGAA GGACTTGGAT TACGTTTCCA CCTCCAAGAC CCAGCTGGTC
CCATCCTCCA AAGATGGGA TGTCAAAGAC ATGCTTTCGC GGGACCGGGA
AACTTCCAGC ATTGAGCCCC TTCCCTCAGA CTCCCCGAAG GAGGAATTAC
GCCCAATTAG GCCCGACACC CCACCCTCCA AACCAGTGGC CTTTGAGGAG
TTTAAGAATG AGCAAGGTAG TGAGATCAAC CGAATTTTCA AAGAAAACAA
ATCCATCTTG AATGAACGGA GGAAAAGGGC CAGCGAGACC ACACAGCACA
TCAATGCCAT CAAGCGGGAG ATTGATGTGA CCAAGGAGGC CCTGAATTTC
CAGAAGTCAC TACGGGAGAA GCAAGGCAAG TACGAAAACA AGGGGCTGAT
GATCATCGAT GAGGAAGAAT TCCTGCTGAT CCTCAAGCTC AAAGACCTCA
AGAAGCAGTA CCGCAGCGAG TACCAGGACC TGCGTGACCT CAGGGCTGAG
ATCCAGTATT GCCAGCACCT AGTGGATCAG TGTCGCCACC GCCTGCTCAT
GGAATTTGAC ATCTGGTACA ATGAGTCCTT TGTCATCCCT GAGGACATGC
AGATGGCACT GAAGCCAGGC GGCAGCATCC GGCCAGGCAT GGTCCCTGTG
AACAGGATTG TGTCTCTGGG AGAAGATGAC CAGGACAAAT TCAGCCAGCT
GCAGCAGAGG GTGCTTCCTG AGGGCCCTGA TTCCATCTCC TTCTACAATG
CCAAAGTCAA GATAGAGCAG AAGCATAATT ACTTGAAAAC CATGATGGGC
CTCCAGCAGG CACATAGAAA ATAGAACCTC ATCGCCA
```

FIG. 2

```
MGTRKKVHAF VRVKPTDDFA HEMIRYGDDK RSIDIHLKKD IRRGVVNNQQ
TDWSFKLDGV LHDASQDLVY ETVAKDVVSQ ALDGYNGTIM CYGQTGAGKT
YTMMGATENY KHRGILPRAL QQVFRMIEER PTHAITVRVS YLEIYNESLF
DLLSTLPYVG PSVTPMTIVE NPQGVFIKGL SVHLTSQEED AFSLLFEGET
NRIIASHTMN KNSSRSHCIF TIYLEAHSRT LSEEKYITSK INLVDLAGSE
RLGKSGSEGQ VLKEATYINK SLSFLEQAII ALGDQKRDHI PFRQCKLTHA
LKDSLGGNCN MVLVTNIYGE AAQLEETLSS LRFASRMKLV TTEPAINEKY
DAERMVKNLE KELALLKQEL AIHDSLTNRT FVTYDPMDEI QIAEINSQVR
RYLEGTLDEI DIISLRQIKE VFNQFRVVLS QQEQEVESTL RRKYTLIDRN
DFAAISAIQK AGLVDVDGHL VGEPEGQNFG LGVAPFSTKP GKKAKSKKTF
KEPLSSLARK EGASSPVNGK DLDYVSTSKT QLVPSSKDGD VKDMLSRDRE
TSSIEPLPSD SPKEELRPIR PDTPPSKPVA FEEFKNEQGS EINRIFKENK
SILNERRKRA SETTQHINAI KREIDVTKEA LNFQKSLREK QGKYENKGLM
IIDEEEFLLI LKLKDLKKQY RSEYQDLRDL RAEIQYCQHL VDQCRHRLLM
EFDIWYNESF VIPEDMQMAL KPGGSIRPGM VPVNRIVSLG EDDQDKFSQL
QQRVLPEGPD SISFYNAKVK IEQKHNYLKT MMGLQQAHRK
```

FIG. 3

```
AGGAAAAAAG TTCATGCATT TGTCCGTGTC AAACCCACCG ATGACTTTGC
TCATGAAATG ATCAGATACG GAGATGACAA AAGAAGCATT GATATTCACT
TAAAAAAAGA CATTCGGAGA GGAGTTGTCA ATAACCAACA GACAGACTGG
TCGTTTAAGT TGGATGGAGT TCTTCACGAT GCCTCCAGG ACTTGGTTTA
TGAGACAGTT GCAAGGATG TGGTTTCTCA GGCCCTCGAT GGCTATAATG
GCACCATCAT GTGTTATGGG CAGACGGGAG CTGGCAAGAC ATACACCATG
ATGGGGGCAA CTGAGAATTA CAAGCACCGG GGGATCCTCC CTCGTGCCCT
GCAGCAGGTT TTTAGGATGA TCGAAGAACG CCCCACACAT GCCATCACTG
TGCGTGTTTC CTACTTGGAA ATCTATAATG AGAGCCTGTT TGATCTCCTG
TCCACTCTGC CCTATGTTGG ACCCTCAGTC ACACCAATGA CCATCGTGGA
AAACCCTCAA GGAGTCTTCA TTAAGGGCTT GTCAGTTCAC CTCACAAGTC
AGGAGGAGGA TGCATTCAGC CTCCTTTTTG AGGGTGAGAC CAACAGGATT
ATAGCCTCCC ACACTATGAA CAAAAACTCT TCCAGATCAC ACTGCATTTT
CACCATCTAC TTAGAGGCCC ATTCCCGGAC CTTATCAGAG GAAAAGTACA
TCACTTCCAA AATTAACTTG GTGGATCTGG CAGGCTCAGA GAGGCTGGGG
AAGTCTGGGT CTGAGGGCCA AGTCCTGAAG GAAGCCACCT ACATCAACAA
ATCGCTCTCA TTCCTGGAGC AGGCCATCAT TGCCCTTGGG GACCAGAAGC
GGGACCACAT CCCCTTTCGG CAGTGCAAGC TCACCCACGC TCTGAAGGAC
TCGTTAGGGG GAAACTGCAA TATGGTCCTC GTGACAAACA TCTATGGAGA
AGCTGCCCAG TTAGAAGAAA CGCTATCTTC ACTGAGATTT GCCAGCAGGA
TGAAGCTAGT CACC
```

FIG. 4

```
RKKVHAF    VRVKPTDDFA   HEMIRYGDDK   RSIDIHLKKD   IRRGVVNNQQ
TDWSFKLDGV LHDASQDLVY   ETVAKDVVSQ   ALDGYNGTIM   CYGQTGAGKT
YTMMGATENY KHRGILPRAL   QQVFRMIEER   PTHAITVRVS   YLEIYNESLF
DLLSTLPYVG PSVTPMTIVE   NPQGVFIKGL   SVHLTSQEED   AFSLLFEGET
NRIIASHTMN KNSSRSHCIF   TIYLEAHSRT   LSEEKYITSK   INLVDLAGSE
RLGKSGSEGQ VLKEATYINK   SLSFLEQAII   ALGDQKRDHI   PFRQCKLTHA
LKDSLGGNCN MVLVTNIYGE   AAQLEETLSS   LRFASRMKLV   TTEPAINEKY
DAERMVKNLE KELALLKQEL   AIHDSLTNRT   FVTYDPMDEI   QIAEINSQVR
```

Fig.5
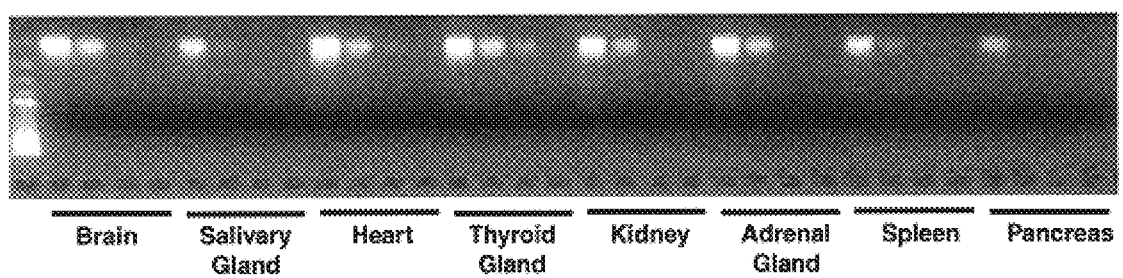
Brain | Salivary Gland | Heart | Thyroid Gland | Kidney | Adrenal Gland | Spleen | Pancreas
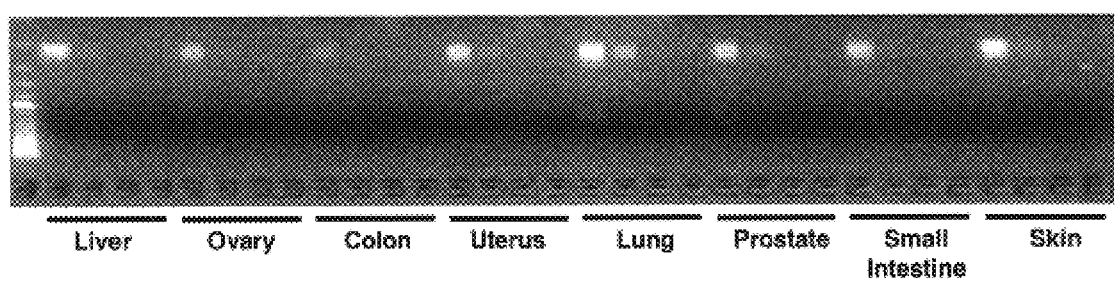
Liver | Ovary | Colon | Uterus | Lung | Prostate | Small Intestine | Skin
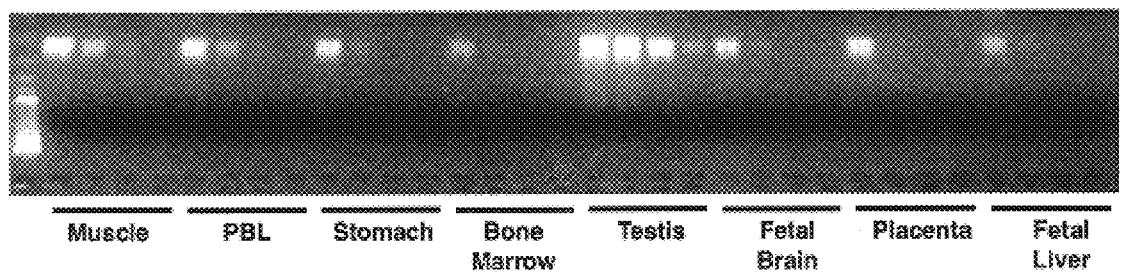
Muscle | PBL | Stomach | Bone Marrow | Testis | Fetal Brain | Placenta | Fetal Liver

SEQUENCE LISTING

<160> NUMBER OF SEQ ID NOS: 4

<210> SEQ ID NO 1
<211> LENGTH: 2387
<212> TYPE: DNA
<213> ORGANISM: Human

<400> SEQUENCE: 1

| | | | | | |
|---|---|---|---|---|---|
| aatgggtact | aggaaaaaag | ttcatgcatt | tgtccgtgtc | aaacccaccg | atgactttgc | 60 |
| tcatgaaatg | atcagatacg | gagatgacaa | agaagcatt | gatattcact | taaaaaaga | 120 |
| cattcggaga | ggagttgtca | ataaccaaca | gacagactgg | tcgtttaagt | tggatggagt | 180 |
| tcttcacgat | gcctcccagg | acttggttta | tgagacagtt | gcaaaggatg | tggtttctca | 240 |
| ggccctcgat | ggctataatg | gcaccatcat | gtgttatggg | cagacgggag | ctggcaagac | 300 |
| atacaccatg | atgggggcaa | ctgagaatta | caagcaccgg | gggatcctcc | ctcgtgccct | 360 |
| gcagcaggtt | tttaggatga | tcgaagaacg | ccccacacat | gccatcactg | tgcgtgtttc | 420 |
| ctacttggaa | atctataatg | agagcctgtt | tgatctcctg | tccactctgc | cctatgttgg | 480 |
| accctcagtc | acaccaatga | ccatcgtgga | aaaccctcaa | ggagtcttca | ttaagggctt | 540 |
| gtcagttcac | ctcacaagtc | aggaggagga | tgcattcagc | ctcctttttg | agggtgagac | 600 |
| caacaggatt | atagcctccc | acactatgaa | caaaaactct | tccagatcac | actgcatttt | 660 |
| caccatctac | ttagaggccc | attcccggac | cttatcagag | gaaaagtaca | tcacttccaa | 720 |
| aattaacttg | gtggatctgg | caggctcaga | gaggctgggg | aagtctgggt | ctgagggcca | 780 |
| agtcctgaag | gaagccacct | acatcaacaa | atcgctctca | ttcctggagc | aggccatcat | 840 |
| tgcccttggg | gaccagaagc | gggaccacat | ccccttcgg | cagtgcaagc | tcacccacgc | 900 |
| tctgaaggac | tcgttagggg | gaaactgcaa | tatggtcctc | gtgacaaaca | tctatggaga | 960 |
| agctgcccag | ttagaagaaa | cgctatcttc | actgagattt | gccagcagga | tgaagctagt | 1020 |
| caccactgag | cctgccatca | atgaaaagta | tgatgctgag | agaatggtca | agaacctgga | 1080 |
| gaaggaacta | gcactactca | agcaggagct | ggctatccat | gacagcctga | ccaaccgcac | 1140 |
| ctttgtgacc | tatgacccca | tggatgaaat | ccagattgct | gagatcaact | cccaggtgcg | 1200 |
| gaggtacctg | gaggggacac | tggacgagat | cgacataatc | agccttagac | agatcaagga | 1260 |
| ggtgttcaac | cagttccggg | tggttctgag | ccaacaggaa | caggaagtgg | agtccactt | 1320 |

-continued

```
gcgcaggaag tacaccctca ttgacaggaa tgactttgca gccatttctg ctatccagaa    1380
ggcgggcctt gtggatgttg atggccacct agtgggtgag cctgaaggac aaaactttgg    1440
actcggagtc gccccttttct ctaccaaacc tgggaagaaa gccaagtcca agaagacatt    1500
caaagagcca ctcagctcct tggcaagaaa ggaaggtgcc agcagccctg tgaatgggaa    1560
ggacttggat tacgttttcca cctccaagac ccagctggtc ccatcctcca agatggggga    1620
tgtcaaagac atgctttcgc gggaccggga aacttccagc attgagcccc ttccctcaga    1680
ctccccgaag gaggaattac gcccaattag gcccgacacc ccaccctcca accagtggc    1740 ctttgaggag tttaagaatg agcaaggtag tgagatcaac cgaattttca agaaaacaa    1800 atccatcttg aatgaacgga ggaaaagggc cagcgagacc acacagcaca tcaatgccat    1860
caagcgggag attgatgtga ccaaggaggc cctgaatttc agaagtcac tacgggagaa    1920 gcaaggcaag tacgaaaaca aggggctgat gatcatcgat gaggaagaat tcctgctgat    1980
cctcaagctc aaagacctca gaagcagta ccgcagcgag taccaggacc tgcgtgacct    2040
cagggctgag atccagtatt gccagcacct agtggatcag tgtcgccacc gcctgctcat    2100
ggaatttgac atctggtaca atgagtcctt tgtcatccct gaggacatgc agatggcact    2160
gaagccaggc ggcagcatcc ggccaggcat ggtccctgtg aacaggattg tgtctctggg    2220
agaagatgac caggacaaat tcagccagct gcagcagagg gtgcttcctg agggccctga    2280
ttccatctcc ttctacaatg ccaaagtcaa gatagagcag aagcataatt acttgaaaac    2340
catgatgggc ctccagcagg cacatagaaa atagaacctc atcgcca                 2387
```

<210> SEQ ID NO 2
<211> LENGTH: 790
<212> TYPE: PRT
<213> ORGANISM: Human

<400> SEQUENCE: 2

```
Met Gly Thr Arg Lys Lys Val His Ala Phe Val Arg Val Lys Pro Thr
 1               5                  10                  15

Asp Asp Phe Ala His Glu Met Ile Arg Tyr Gly Asp Asp Lys Arg Ser
                20                  25                  30

Ile Asp Ile His Leu Lys Lys Asp Ile Arg Arg Gly Val Val Asn Asn
            35                  40                  45

Gln Gln Thr Asp Trp Ser Phe Lys Leu Asp Gly Val Leu His Asp Ala
        50                  55                  60

Ser Gln Asp Leu Val Tyr Glu Thr Val Ala Lys Asp Val Val Ser Gln
65                  70                  75                  80

Ala Leu Asp Gly Tyr Asn Gly Thr Ile Met Cys Tyr Gly Gln Thr Gly
                85                  90                  95

Ala Gly Lys Thr Tyr Thr Met Met Gly Ala Thr Glu Asn Tyr Lys His
            100                 105                 110

Arg Gly Ile Leu Pro Arg Ala Leu Gln Gln Val Phe Arg Met Ile Glu
        115                 120                 125

Glu Arg Pro Thr His Ala Ile Thr Val Arg Val Ser Tyr Leu Glu Ile
    130                 135                 140

Tyr Asn Glu Ser Leu Phe Asp Leu Leu Ser Thr Leu Pro Tyr Val Gly
145                 150                 155                 160

Pro Ser Val Thr Pro Met Thr Ile Val Glu Asn Pro Gln Gly Val Phe
                165                 170                 175

Ile Lys Gly Leu Ser Val His Leu Thr Ser Gln Glu Glu Asp Ala Phe
            180                 185                 190
```

```
Ser Leu Leu Phe Glu Gly Glu Thr Asn Arg Ile Ile Ala Ser His Thr
            195                 200                 205

Met Asn Lys Asn Ser Ser Arg Ser His Cys Ile Phe Thr Ile Tyr Leu
            210                 215                 220

Glu Ala His Ser Arg Thr Leu Ser Glu Glu Lys Tyr Ile Thr Ser Lys
225                 230                 235                 240

Ile Asn Leu Val Asp Leu Ala Gly Ser Glu Arg Leu Gly Lys Ser Gly
                245                 250                 255

Ser Glu Gly Gln Val Leu Lys Glu Ala Thr Tyr Ile Asn Lys Ser Leu
            260                 265                 270

Ser Phe Leu Glu Gln Ala Ile Ile Ala Leu Gly Asp Gln Lys Arg Asp
            275                 280                 285

His Ile Pro Phe Arg Gln Cys Lys Leu Thr His Ala Leu Lys Asp Ser
            290                 295                 300

Leu Gly Gly Asn Cys Asn Met Val Leu Val Thr Asn Ile Tyr Gly Glu
305                 310                 315                 320

Ala Ala Gln Leu Glu Glu Thr Leu Ser Ser Leu Arg Phe Ala Ser Arg
                325                 330                 335

Met Lys Leu Val Thr Thr Glu Pro Ala Ile Asn Glu Lys Tyr Asp Ala
            340                 345                 350

Glu Arg Met Val Lys Asn Leu Glu Lys Glu Leu Ala Leu Leu Lys Gln
            355                 360                 365

Glu Leu Ala Ile His Asp Ser Leu Thr Asn Arg Thr Phe Val Thr Tyr
            370                 375                 380

Asp Pro Met Asp Glu Ile Gln Ile Ala Glu Ile Asn Ser Gln Val Arg
385                 390                 395                 400

Arg Tyr Leu Glu Gly Thr Leu Asp Glu Ile Asp Ile Ile Ser Leu Arg
                405                 410                 415

Gln Ile Lys Glu Val Phe Asn Gln Phe Arg Val Val Leu Ser Gln Gln
            420                 425                 430

Glu Gln Glu Val Glu Ser Thr Leu Arg Arg Lys Tyr Thr Leu Ile Asp
            435                 440                 445

Arg Asn Asp Phe Ala Ala Ile Ser Ala Ile Gln Lys Ala Gly Leu Val
450                 455                 460

Asp Val Asp Gly His Leu Val Gly Glu Pro Glu Gly Gln Asn Phe Gly
465                 470                 475                 480

Leu Gly Val Ala Pro Phe Ser Thr Lys Pro Gly Lys Lys Ala Lys Ser
                485                 490                 495

Lys Lys Thr Phe Lys Glu Pro Leu Ser Ser Leu Ala Arg Lys Glu Gly
            500                 505                 510

Ala Ser Ser Pro Val Asn Gly Lys Asp Leu Asp Tyr Val Ser Thr Ser
            515                 520                 525

Lys Thr Gln Leu Val Pro Ser Ser Lys Asp Gly Asp Val Lys Asp Met
            530                 535                 540

Leu Ser Arg Asp Arg Glu Thr Ser Ser Ile Glu Pro Leu Pro Ser Asp
545                 550                 555                 560

Ser Pro Lys Glu Glu Leu Arg Pro Ile Arg Pro Asp Thr Pro Pro Ser
                565                 570                 575

Lys Pro Val Ala Phe Glu Glu Phe Lys Asn Glu Gln Gly Ser Glu Ile
            580                 585                 590

Asn Arg Ile Phe Lys Glu Asn Lys Ser Ile Leu Asn Glu Arg Arg Lys
            595                 600                 605
```

-continued

| Arg | Ala | Ser | Glu | Thr | Thr | Gln | His | Ile | Asn | Ala | Ile | Lys | Arg | Glu | Ile |
| | | 610 | | | | 615 | | | | 620 | | | | | |

| Asp | Val | Thr | Lys | Glu | Ala | Leu | Asn | Phe | Gln | Lys | Ser | Leu | Arg | Glu | Lys |
| 625 | | | | | 630 | | | | 635 | | | | | 640 | |

| Gln | Gly | Lys | Tyr | Glu | Asn | Lys | Gly | Leu | Met | Ile | Ile | Asp | Glu | Glu | Glu |
| | | | | 645 | | | | 650 | | | | | 655 | | |

| Phe | Leu | Leu | Ile | Leu | Lys | Leu | Lys | Asp | Leu | Lys | Lys | Gln | Tyr | Arg | Ser |
| | | | 660 | | | | 665 | | | | 670 | | | | |

| Glu | Tyr | Gln | Asp | Leu | Arg | Asp | Leu | Arg | Ala | Glu | Ile | Gln | Tyr | Cys | Gln |
| | | | 675 | | | | 680 | | | | | 685 | | | |

| His | Leu | Val | Asp | Gln | Cys | Arg | His | Arg | Leu | Leu | Met | Glu | Phe | Asp | Ile |
| | 690 | | | | | 695 | | | | | 700 | | | | |

| Trp | Tyr | Asn | Glu | Ser | Phe | Val | Ile | Pro | Glu | Asp | Met | Gln | Met | Ala | Leu |
| 705 | | | | | 710 | | | | | 715 | | | | | 720 |

| Lys | Pro | Gly | Gly | Ser | Ile | Arg | Pro | Gly | Met | Val | Pro | Val | Asn | Arg | Ile |
| | | | | 725 | | | | | 730 | | | | | 735 | |

| Val | Ser | Leu | Gly | Glu | Asp | Asp | Gln | Asp | Lys | Phe | Ser | Gln | Leu | Gln | Gln |
| | | | 740 | | | | | 745 | | | | | 750 | | |

| Arg | Val | Leu | Pro | Glu | Gly | Pro | Asp | Ser | Ile | Ser | Phe | Tyr | Asn | Ala | Lys |
| | | | 755 | | | | 760 | | | | | 765 | | | |

| Val | Lys | Ile | Glu | Gln | Lys | His | Asn | Tyr | Leu | Lys | Thr | Met | Met | Gly | Leu |
| | 770 | | | | | 775 | | | | | 780 | | | | |

| Gln | Gln | Ala | His | Arg | Lys |
| 785 | | | | | 790 |

<210> SEQ ID NO 3
<211> LENGTH: 1014
<212> TYPE: DNA
<213> ORGANISM: Human

<400> SEQUENCE: 3

```
aggaaaaaag ttcatgcatt tgtccgtgtc aaacccaccg atgactttgc tcatgaaatg      60
atcagatacg gagatgacaa agaagcatt gatattcact aaaaaaaga cattcggaga      120
ggagttgtca ataaccaaca gacagactgg tcgtttaagt tggatggagt tcttcacgat     180
gcctcccagg acttggttta tgagacagtt gcaaaggatg tggtttctca ggccctcgat     240
ggctataatg caccatcat gtgttatggg cagacgggag ctggcaagac atacaccatg     300
atggggcaa ctgagaatta caagcaccgg gggatcctcc ctcgtgccct gcagcaggtt     360
tttaggatga tcgaagaacg ccccacacat gccatcactg tgcgtgtttc ctacttggaa     420
atctataatg agagcctgtt tgatctcctg tccactctgc cctatgttgg accctcagtc     480
acaccaatga ccatcgtgga aaaccctcaa ggagtcttca ttaagggctt gtcagttcac     540
ctcacaagtc aggaggagga tgcattcagc ctccttttg agggtgagac caacaggatt     600
atagcctccc acactatgaa caaaaactct tccagatcac actgcatttt caccatctac     660
ttagaggccc attcccggac cttatcagag gaaaagtaca tcacttccaa aattaacttg     720
gtggatctgg caggctcaga gaggctgggg aagtctgggt ctgagggcca gtcctgaag      780
gaagccacct acatcaacaa atcgctctca ttcctggagc aggccatcat tgcccttggg     840
gaccagaagc gggaccacat ccccttttcgg cagtgcaagc tcacccacgc tctgaaggac    900
tcgttagggg gaaactgcaa tatggtcctc gtgacaaaca tctatggaga agctgcccag    960
ttagaagaaa cgctatcttc actgagattt gccagcagga tgaagctagt cacc         1014
```

-continued

```
<210> SEQ ID NO 4
<211> LENGTH: 338
<212> TYPE: PRT
<213> ORGANISM: Human

<400> SEQUENCE: 4

Arg Lys Lys Val His Ala Phe Val Arg Val Lys Pro Thr Asp Asp Phe
 1               5                  10                  15

Ala His Glu Met Ile Arg Tyr Gly Asp Asp Lys Arg Ser Ile Asp Ile
                20                  25                  30

His Leu Lys Lys Asp Ile Arg Arg Gly Val Val Asn Asn Gln Gln Thr
             35                  40                  45

Asp Trp Ser Phe Lys Leu Asp Gly Val Leu His Asp Ala Ser Gln Asp
         50                  55                  60

Leu Val Tyr Glu Thr Val Ala Lys Asp Val Val Ser Gln Ala Leu Asp
 65                  70                  75                  80

Gly Tyr Asn Gly Thr Ile Met Cys Tyr Gly Gln Thr Gly Ala Gly Lys
                 85                  90                  95

Thr Tyr Thr Met Met Gly Ala Thr Glu Asn Tyr Lys His Arg Gly Ile
                100                 105                 110

Leu Pro Arg Ala Leu Gln Gln Val Phe Arg Met Ile Glu Glu Arg Pro
            115                 120                 125

Thr His Ala Ile Thr Val Arg Val Ser Tyr Leu Glu Ile Tyr Asn Glu
        130                 135                 140

Ser Leu Phe Asp Leu Leu Ser Thr Leu Pro Tyr Val Gly Pro Ser Val
145                 150                 155                 160

Thr Pro Met Thr Ile Val Glu Asn Pro Gln Gly Val Phe Ile Lys Gly
                165                 170                 175

Leu Ser Val His Leu Thr Ser Gln Glu Glu Asp Ala Phe Ser Leu Leu
            180                 185                 190

Phe Glu Gly Glu Thr Asn Arg Ile Ile Ala Ser His Thr Met Asn Lys
        195                 200                 205

Asn Ser Ser Arg Ser His Cys Ile Phe Thr Ile Tyr Leu Glu Ala His
    210                 215                 220

Ser Arg Thr Leu Ser Glu Glu Lys Tyr Ile Thr Ser Lys Ile Asn Leu
225                 230                 235                 240

Val Asp Leu Ala Gly Ser Glu Arg Leu Gly Lys Ser Gly Ser Glu Gly
                245                 250                 255

Gln Val Leu Lys Glu Ala Thr Tyr Ile Asn Lys Ser Leu Ser Phe Leu
            260                 265                 270

Glu Gln Ala Ile Ile Ala Leu Gly Asp Gln Lys Arg Asp His Ile Pro
        275                 280                 285

Phe Arg Gln Cys Lys Leu Thr His Ala Leu Lys Asp Ser Leu Gly Gly
    290                 295                 300

Asn Cys Asn Met Val Leu Val Thr Asn Ile Tyr Gly Glu Ala Ala Gln
305                 310                 315                 320

Leu Glu Glu Thr Leu Ser Ser Leu Arg Phe Ala Ser Arg Met Lys Leu
                325                 330                 335

Val Thr
```

MOTOR PROTEINS AND METHOD FOR THEIR USE

This application is a continuation of Ser. No. 09/634,957, filed Aug. 8, 2000, the disclosure of which is incorporated by reference.

FIELD OF THE INVENTION

The invention provides isolated nucleic acid and amino acid sequences of HsKif9, methods of detecting HsKif9 and screening for HsKif9 modulators using biologically active HsKif9, and kits for screening for HsKif9 modulators.

BACKGROUND OF THE INVENTION

The kinesin superfamily is an extended family of related microtubule motor proteins. It can be classified into at least 8 subfamilies based on primary amino acid sequence, domain structure, velocity of movement, and cellular function. This family is exemplified by "true" kinesin, which was first isolated from the axoplasm of squid, where it is believed to play a role in anterograde axonal transport of vesicles and organelles (see, e.g., Goldstein, *Annu. Rev. Genet.* 27:319–351 (1993)). Kinesin uses ATP to generate force and directional movement associated with microtubules.

Within this functional group of kinesins resides a group of kinesins from several organisms that share significant sequence homology, including mouse kinesin Kif9. See, Nakagawa et al. (1997) Proc. Natl. Acad. Sci. USA 94:9654–9659; GenBank Accession Number AB001437, and GenBank Accession Number BAA22397 each of which is incorporated herein by reference for all purposes.

The discovery of a new kinesin motor protein which is the human ortholog of mouse kinesin Kif9, and the polynucleotides encoding it satisfies a need in the art by providing new compositions which are useful in the diagnosis, prevention, and treatment of cancer, neurological disorders, and disorders of vesicular transport.

SUMMARY OF THE INVENTION

The present invention is based on the discovery of a new human kinesin motor protein, HsKif9, the polynucleotide encoding HsKif9, and the use of these compositions for the diagnosis, treatment, or prevention of cancer, neurological disorders, and disorders of vesicular transport.

In one aspect, the invention provides an isolated nucleic acid sequence encoding a kinesin superfamily motor protein, wherein the motor protein has the following properties: (i) the protein's activity includes microtubule stimulated ATPase activity; and (ii) the protein has a sequence that has greater than 70%, 80%, or 90% amino acid sequence identity to SEQ ID NO:2 or SEQ ID NO:4 as measured using a sequence comparison algorithm. In one embodiment, the protein further specifically binds to polyclonal antibodies raised against SEQ ID NO:2 or SEQ ID NO:4.

In one embodiment, the nucleic acid encodes HsKif9 or a fragment thereof. In another embodiment, the nucleic acid encodes SEQ ID NO:2 or SEQ ID NO:4. In another embodiment, the nucleic acid has a nucleotide sequence of SEQ ID NO: 1 or SEQ ID NO:3.

In one aspect, the nucleic acid comprises a sequence which encodes an amino acid sequence which has greater than 70% sequence identity with SEQ ID NO:2 or SEQ ID NO:4, preferably greater than 80%, more preferably greater than 90%, more preferably greater than 95% or, in another embodiment, has 98 to 100% sequence identity with SEQ ID NO:2 or SEQ ID NO:4.

In one embodiment, the nucleic acid comprises a sequence which has greater than 55 or 60% sequence identity with SEQ ID NO: 1 or SEQ ID NO:3, preferably greater than 70%, more preferably greater than 80%, more preferably greater than 90 or 95% or, in another embodiment, has 98 to 100% sequence identity with SEQ ID NO:1 or SEQ ID NO:3. In another embodiment provided herein, the nucleic acid hybridizes under stringent conditions to a nucleic acid having a sequence or complementary sequence of SEQ ID NO:1 or SEQ ID NO:3.

In another aspect, the invention provides an expression vector comprising a nucleic acid encoding a kinesin superfamily motor protein, wherein the motor protein has the following properties: (i) the protein's activity includes microtubule stimulated ATPase activity; and (ii) the protein has a sequence that has greater than 70, 80, or 90% amino acid sequence identity to SEQ ID NO:2 or SEQ ID NO:4 as measured using a sequence comparison algorithm. The invention further provides a host cell transfected with the vector.

In another aspect, the invention provides an isolated kinesin superfamily motor protein, wherein the protein has one or more of the properties described above. In one embodiment, the protein specifically binds to polyclonal antibodies generated against a motor domain, tail domain or other fragment of HsKif9. In another embodiment, the protein comprises an amino acid sequence of SEQ ID NO:2 or SEQ ID NO:4.

In one aspect, the protein provided herein comprises an amino acid sequence which has greater than 70% sequence identity with SEQ ID NO:2 or SEQ ID NO:4, preferably greater than 80%, more preferably greater than 90%, more preferably greater than 95% or, in another embodiment, has 98 to 100% sequence identity with SEQ ID NO:2 or SEQ ID NO:4.

The invention features a substantially purified polypeptide comprising the amino acid sequence of SEQ ID NO:2 or SEQ ID NO:4 or a fragment thereof and more particularly, the motor domain of the amino acid sequence of SEQ ID NO:2 or SEQ ID NO:4 or a fragment thereof.

In one embodiment, the present invention provides a method of identifying a candidate gent as a modulator of the activity of a target protein. The method comprises adding a candidate agent to a mixture comprising a target protein which directly or indirectly produces ADP or phosphate, under conditions that normally allow the production of ADP or phosphate. The method further comprises subjecting the mixture to a reaction that uses said ADP or phosphate as a substrate under conditions that normally allow the ADP or phosphate to be utilized and determining the level of activity of the reaction as a measure of the concentration of ADP or phosphate. A change in the level between the presence and absence of the candidate agent indicates a modulator of the target protein.

The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate.

Preferably, the target protein either directly or indirectly produces ADP or phosphate and comprises a motor domain. More preferably, the target protein comprises a kinesin superfamily motor protein as described above and most preferably, the target protein comprises HsKif9 or a fragment thereof.

Also provided are modulators of the target protein including agents for the treatment of cellular proliferation, including cancer, hyperplasias, restenosis, cardiac hypertrophy, immune disorders and inflammation. The agents and compositions provided herein can be used in variety of applications which include the formulation of sprays, powders, and other compositions. Also provided herein are methods of treating cellular proliferation disorders such as cancer, hyperplasias, restenosis, cardiac hypertrophy, immune disorders and inflammation, for treating disorders associated with HsKif9 activity, and for inhibiting HsKif9.

BRIEF DESCRIPTION OF THE DRAWINGS

FIG. 1 shows an embodiment of a nucleic acid sequence encoding HsKif9 (SEQ ID NO:1).

FIG. 2 shows the amino acid sequence of HsKif9 (SEQ ID NO:2).

FIG. 3 shows an embodiment of a nucleic acid sequence encoding the motor domain of HsKif9 (SEQ ID NO:3).

FIG. 4 shows the amino acid sequence of the motor domain of HsKif9 (SEQ ID NO:4).

FIG. 5 shows the qualitative tissue expression profile of HsKif9.

DETAILED DESCRIPTION OF THE INVENTION

I. Definitions

"ADP" refers to adenosine diphosphate and also includes ADP analogs, including, but not limited to, deoxyadenosine diphosphate (dADP) and adenosine analogs. "Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term antibody also includes antibody fragments either produced by the modification of whole antibodies or those synthesized de novo using recombinant DNA methodologies.

An "anti-HsKif9" antibody is an antibody or antibody fragment that specifically binds a polypeptide encoded by the HsKif9 gene, cDNA, or a subsequence thereof. "Biologically active" target protein refers to a target protein that has one or more of kinesin protein's biological activities, including, but not limited to microtubule stimulated ATPase activity, as tested, e.g., in an ATPase assay. Biological activity can also be demonstrated in a microtubule gliding assay or a microtubule binding assay. "ATPase activity" refers to ability to hydrolyze ATP. Other activities include polymerization/depolymerization (effects on microtubule dynamics), binding to other proteins of the spindle, binding to proteins involved in cell-cycle control, or serving as a substrate to other enzymes, such as kinases or proteases and specific kinesin cellular activities, such as chromosome congregation, axonal transport, etc.

"Biological sample" as used herein is a sample of biological tissue or fluid that contains a target protein or a fragment thereof or nucleic acid encoding a target protein or a fragment thereof. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc. Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each degenerate codon in a nucleic acid can be modified to yield a functionally identical molecule. Accordingly, each silent variation of a nucleic acid which encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, intermediate filaments, myosin fragments), molecular motors (e.g., kinesins, myosins, dyneins), cytoskeleton associated regulatory proteins (e.g., tropomysin, alpha-actinin) and cytoskeletal associated binding proteins (e.g., microtubules associated proteins, actin binding proteins).

"Cytoskeletal function" refers to biological roles of the cytoskeleton, including but not limited to the providing of structural organization (e.g., microvilli, mitotic spindle) and the mediation of motile events within the cell (e.g., muscle contraction, mitotic chromosome movements, contractile ring formation and function, pseudopodal movement, active cell surface deformations, vesicle formation and translocation.)

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay which provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is 50 or 100 amino acids in length. This definition also refers to the complement of a test sequence, provided that the test sequence has a designated or substantial identity to a reference sequence. Preferably, the percent identity exists over a region of the sequence that is at least about 25 nucleotides in length, more preferably over a region that is 50 or 100 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, e.g., the algorithm of Meyers & Millers, Computer Applic. Biol. Sci. 4:11–17 (1988), e.g., as implemented in the program PC/GENE (Intelligenetics, Mountain View, Calif.).

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated gene, the nucleic acid of interest is separated from open reading frames which flank the gene of interest and encode proteins other than the protein of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

A "labeled nucleic acid probe or oligonucleotide" is one that is bound, either covalently, through a linker, or through ionic, van der Waals, or hydrogen bonds to a label such that the presence of the probe may be detected by detecting the presence of the label bound to the probe.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assays for target protein activity. Such assays include ATPase activity, microtubule gliding, microtubule depolymerizing activity, and binding activity such as microtubule binding activity or binding of nucleotide analogs. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Molecular motor" refers to a molecule that utilizes chemical energy to generate mechanical force. According to one embodiment, the molecular motor drives the motile properties of the cytoskeleton.

The phrase "motor domain" refers to the domain of a target protein that confers membership in the kinesin superfamily of motor proteins through a sequence identity of approximately 35–45% identity to the motor domain of true kinesin.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidine complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A target protein comprises a polypeptide demonstrated to have at least microtubule stimulated ATPase activity. Amino acids may be referred to herein by either their commonly known three letter symbols or by Nomenclature Commission. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA box element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to HsKif9 with the amino acid sequence encoded in SEQ ID NO:2 can be selected to obtain only those antibodies that are specifically immunoreactive with HsKif9 and not with other proteins, except for polymorphic variants, orthologs, alleles, and closely related homologues of HsKif9. This selection may be achieved by subtracting out antibodies that cross react with molecules, for example, such as C. elegans unc-104 and human KiflA. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound which is believed to be capable of modulating the cytoskeletal system in vivo which can have application in both human and animal disease. Modulation of the cytoskeletal system would be desirable in a number of conditions including, but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal wound healing, inflammatory and immune disorders such as rheumatoid arthritis, Bechet's disease, gout or gouty arthritis, abnormal angiogenesis accompanying: rheumatoid arthritis, psoriasis, diabetic retinopathy, and other ocular angiogenic disesase such as, macular degeneration, corneal graft rejection, corneal overgrowth, glaucoma, and Osler Webber syndrome.

II. The Target Protein

The present invention provides for the first time a nucleic acid encoding HsKif9. This protein is a member of the kinesin superfamily of motor proteins. More specifically, the HsKif9 sequence of FIG. 2 shares approximately 89% identity to the mouse Kif9. See Nakagawa et al. (1997) Proc. Natl. Acad. Sci. USA 94:9654–9.

In one aspect, HsKif9 can be defined by having at least one or preferably more than one of the following functional and structural characteristics. Functionally, HsKif9 will have microtubule-stimulated ATPase activity, and microtubule motor activity that is ATP dependent. HsKif9 activity can also be described in terms of its ability to bind microtubules.

The novel nucleotides sequences provided herein encode HsKif9 or fragments thereof. Thus, in one aspect, the nucleic acids provided herein are defined by the novel proteins provided herein. The protein provided herein comprises an amino acid sequence which has one or more of the following characteristics: greater than 70% sequence identity with SEQ ID NO:2 or SEQ ID NO:4, preferably greater than 80%, more preferably greater than 90%, more preferably greater than 95% or, in another embodiment, has 98 to 100% sequence identity with SEQ ID NO:2 or SEQ ID NO:4. As described above, when describing the nucleotide in terms of SEQ ID NO:1 or SEQ ID NO:3, the sequence identity may be slightly lower due to the degeneracy in the genetic code. Also included within the definition of the target proteins are amino acid sequence variants of wild-type target proteins.

Portions of the HsKif9 nucleotide sequence may be used to identify polymorphic variants, orthologs, alleles, and homologues of HsKif9. This identification can be made in vitro, e.g., under stringent hybridization conditions and sequencing, or by using the sequence information in a computer system for comparison with other nucleotide sequences. Sequence comparison can be performed using any of the sequence comparison algorithms discussed below, with PILEUP as a preferred algorithm.

As will be appreciated by those in the art, the target proteins can be made in a variety of ways, including both synthesis de novo and by expressing a nucleic acid encoding the protein.

Target proteins of the present invention may also be modified in a way to form chimeric molecules comprising a fusion of a target protein with a tag polypeptide which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393.

The biological activity of any of the peptides provided herein can be routinely confirmed by the assays provided herein such as those which assay ATPase activity or microtubule binding activity. In one embodiment, polymorphic variants, alleles, and orthologs, homologues of HsKif9 are confirmed by using a ATPase or microtubule binding assays as known in the art.

The isolation of biologically active HsKif9 for the first time provides a means for assaying for modulators of this kinesin superfamily protein. Biologically active HsKif9 is useful for identifying modulators of HsKif9 or fragments thereof and kinesin superfamily members using in vitro assays such as microtubule gliding assays, ATPase assays (Kodama et al., J Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)). In vivo assays and uses are provided herein as well. Also provided herein are methods of identifying candidate agents which bind to HsKif9 and portions thereof.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, agricultural and research based applications.

III. Isolation of the gene encoding HsKif9
A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from mass spectroscopy, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonculeotides is by either native acrylamide gel electrophoresis or by anion-exchange HPLC as described in Pearson & Reanier, *J. Chrom.* 225:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding HsKif9

In general, the nucleic acid sequences encoding HsKif9 and related nucleic acid sequence homologs are cloned from cDNA and genomic DNA libraries or isolated using amplification techniques with oligonucleotide primers. Alternatively, expression libraries can be used to clone HsKif9 and HsKif9 homologues by detected expressed homologues immunologically with antisera or purified antibodies made against HsKif9 that also recognize and selectively bind to the HsKif9 homologue. Finally, amplification techniques using primers can be used to amplify and isolate HsKif9 from DNA or RNA. Amplification techniques using degenerate primers can also be used to amplify and isolate HsKif9 homologues. Amplification techniques using primers can also be used to isolate a nucleic acid encoding HsKif9. These primers can be used, e.g., to amplify a probe of several hundred nucleotides, which is then used to screen a library for full-length HsKif9.

Appropriate primers and probes for identifying the gene encoding homologues of HsKif9 in other species are generated from comparisons of the sequences provided herein. As described above, antibodies can be used to identify HsKif9 homologues. For example, antibodies made to the motor domain of HsKif9 or to the whole protein are useful for identifying HsKif9 homlogues.

To make a cDNA library, one should choose a source that is rich in the mRNA of choice, e.g., HsKif9. For example, HsKif9 mRNA is overexpressed in testes. See FIG. 5. The mRNA is then made into cDNA using reverse transcriptase, ligated into a recombinant vector, and introduced into a recombinant host for propagation, screening and cloning. Methods for making and screening cDNA libraries are well known (see, e.g., Gubler & Hoffman, Gene 25: 263–269); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180–182 (1977). Colony hybridization is read out as generally described in Grunstein et al., Proc. Natl. Acad. Sci. USA, 72:3961–3965 (1975).

An alternative method of isolating HsKif9 nucleic acid and its homologues combines the use of synthetic oligonucleotide primers and amplification of an RNA or DNA template (see U.S. Pat. Nos. 4,683,195 and 4,683,202; PCR Protocols: A guide to Methods and Applications (Innis et al., eds. 1990)). Methods such as polymerase chain reaction and ligase chain reaction can be used to amplify nucleic acid sequences of HsKif9 directly from mRNA, from cDNA, from genomic libraries or cDNA libraries. Degenerate oligonucleotides can be designed to amplify HsKif9 homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of HsKif9 encoding mRNA in physiological samples, for nucleic sequencing or for other purposes. Genes amplified by the PCR reaction can be purified from agarose gels and cloned into an appropriate vector.

Gene expression of HsKif9 can also be analyzed by techniques known in the art, e.g., reverse transcription and amplification of mRNA, isolation of total RNA or poly A+RNA, northern blotting, dot blotting, in situ hybridization, RNase protection, quantitative PCR, and the like.

Synthetic oligonucleotides can be used to construct recombinant HsKif9 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the HsKif9 gene. The specific subsequence is then ligated into an expression vector.

The gene for HsKif9 is typically cloned into intermediate vectors before transformation into prokaryotic or eukaryotic cells for replication and/or expression. The intermediate vectors are typically prokaryote vectors or shuttle vectors.

C. Expression in Prokaryotes and Eukaryotes

To obtain high level expression of a cloned gene, such as those cDNAs encoding HsKif9, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the HsKif9 protein are available in, e.g., *E. coli, Bacillus sp.*, and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. The pET expression system (Novagen) is a preferred prokaryotic expression system.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the HsKif9 encoding nucleic acid in host cells. A typical expression cassette thus contains a promoter operably linked to the nucleic acid sequence encoding HsKif9 and signals required for efficient polyadenylation of the transcript, ribosome binding sites, and translation termination. The nucleic acid sequence encoding HsKif9 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23, and fusion expression systems such as GST and LacZ. Epitope tags can also be added to recombinant proteins to provide convenient methods of isolation, e.g., c-myc or histidine tags.

Expression vectors containing regulatory elements from eukaryotic viruses are typically used in eukaryotic expression vectors, e.g., SV40 vectors, cytomegalovirus vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a HsKif9 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection or transformation methods are used to produce bacterial, mammalian, yeast or insect cell lines that express large quantities of HsKif9 protein, which are then purified using standard techniques (see, e.g., Colley et al., *J. Biol. Chem.* 264:17619–17622 (1989); *Guide to Protein Purification, in Methods in Enzymology*, vol. 182 (Deutscher ed., 1990)).

Transformation of eukaryotic and prokaryotic cells are performed according to standard techniques (see, e.g., Morrison, *J. Bact.*, 132:349–351 (1977); Clark-Curtiss & Curtiss, *Methods in Enzymology*, 101:347–362 (Wu et al., eds, 1983). Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing HsKif9.

After the expression vector is introduced into the cells, the transfected cells are cultured under conditions favoring expression of HsKif9, which is recovered from the culture using standard techniques identified below.

IV. Purification of HsKif9 Protein

Either naturally occurring or recombinant HsKif9 can be purified for use in functional assays. In a preferred embodiment, the target proteins are purified for use in the assays to provide substantially pure samples. Alternatively, the target protein need not be substantially pure as long as the sample comprising the target protein is substantially free of other components that can contribute to the production of ADP or phosphate.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography, chromatofocussing, selective precipitation with such substances as ammonium sulfate;and others (see, e.g., Scopes, Protein Purification: Principles and Practice (1982); U.S. Pat. No. 4,673,641; Ausubel et al. supra; and Sambrook et al., supra). For example, the target protein can be purified using a standard anti-target antibody column. Ultrafiltration and diafiltration techniques, in conjunction with protein concentration, are also useful. A preferred method of purification is use of Ni-NTA agarose (Qiagen).

The expressed protein can be purified by standard chromatographic procedures to yield a purified, biochemically active protein. The activity of any of the peptides provided herein can be routinely confirmed by the assays provided herein such as those which assay ATPase activity or microtubule binding activity. Biologically active target protein is useful for identifying modulators of target protein or fragments thereof and kinesin superfamily members using in vitro assays such as microtubule gliding assays, ATPase assays (Kodama et al., J. Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)), as described in detail below.

A. Purification of HsKif9 from Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein. Alternatively, it is possible to purify HsKif9 from bacteria periplasm. After HsKif9 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Suitable purification schemes for some specific kinesins are outlined in U.S. Ser. No. 09/295,612, filed Apr. 20, 1999, hereby expressly incorporated herein in its entirety for all purposes.

B. Standard Protein Separation Techniques For Purifying HsKif9

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diaflitration. Other methods that rely on solubility of proteins, such as cold ethanol precipitation, are well known to those of skill in the art and can be used to fractionate complex protein mixtures.

Size Differential Filtration

The molecular weight of HsKif9 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

HsKif9 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of HsKif9

In addition to the detection of HsKif9 genes and gene expression using nucleic acid hybridization technology, one can also use immunoassays to detect HsKif9. Imunoassays can be used to qualitatively or quantitatively analyze HsKif9. A general overview of the applicable technology can be found in Harlow & Lane, *Antibodies: A Laboratory Manual* (1988).

A. Antibodies to HsKif9

Methods of producing polyclonal and monoclonal antibodies that react specifically with HsKif9 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of HsKif9 comprising immunogens may be used to produce antibodies specifically reactive with HsKif9. For example, recombinant HsKif9 or a antigenic fragment thereof such as the motor domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immnunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to HsKif9. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-HsKif9 proteins or even other homologous proteins from other organisms (e.g., *C. elegans* unc-104 or human KiflA), using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

Once HsKif9 specific antibodies are available, HsKif9 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio ed., 1980); and Harlow & Lane, supra.

B. Binding Assays

Antibodies can be used for treatment or to identify the presence of HsKif9 having the sequence identity characteristics as described herein. Additionally, antibodies can be used to identify modulators of the interaction between the antibody and HsKif9 as further described below. While the following discussion is directed toward the use of antibodies in the use of binding assays, it is understood that the same general assay formats such as those described for "non-competitive" or "competitive" assays can be used with any compound which binds to HsKif9 such as microtubules or the compounds described in U.S. Ser. No. 60/070,772.

In a preferred embodiment, HsKif9 is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37. *Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the HsKif9 or antigenic subsequence thereof). The antibody (e.g., anti-HsKif9) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled HsKif9 polypeptide or a labeled anti-HsKif9 antibody. Alternatively, the labeling agent may be a third moiety, such a secondary antibody, that specifically binds to the antibody/HsKif9 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol.* 111:1401–1406(1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 4° C. to 40° C.

Non-Competitive Assay Formats

Immunoassays for detecting HsKif9 in samples may be either competitive or noncompetitive. Noncompetitive immunoassays are assays in which the amount of antigen is directly measured. In one preferred "sandwich" assay, for example, the anti-HsKif9 antibodies can be bound directly to a solid substrate on which they are immobilized. These immobilized antibodies then capture HsKif9 present in the test sample. HsKif9 is thus immobilized is then bound by a labeling agent, such as a second HsKif9 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of HsKif9 present in the sample is measured indirectly by measuring the amount of a known, added (exogenous) HsKif9 displaced (competed away) from an anti-HsKif9 antibody by the unknown HsKif9 present in a sample. In one competitive assay, a known amount of HsKif9 is added to a sample and the sample is then contacted with an antibody that specifically binds to HsKif9. The amount of exogenous HsKif9 bound to the antibody is inversely proportional to the concentration of HsKif9 present in the sample. In a particularly preferred embodiment, the antibody is immobilized on a solid substrate. The amount of HsKif9 bound to the antibody may be determined either by measuring the amount of HsKif9 present in a HsKif9/antibody complex, or alternatively by measuring the amount of remaining uncomplexed protein. The amount of HsKif9 may be detected by providing a labeled HsKif9 molecule.

A hapten inhibition assay is another preferred competitive assay. In this assay the known HsKif9, is immobilized on a solid substrate. A known amount of anti-HsKif9 antibody is added to the sample, and the sample is then contacted with the HsKif9. The amount of anti-HsKif9 antibody bound to the known immobilized HsKif9 is inversely proportional to the amount of HsKif9 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, a protein at least partially encoded by SEQ ID NO:2 can be immobilized to a solid support. Proteins (e.g., C. elegans unc-104 or human Kif1A) are added to the assay that compete for binding of the antisera to the immobilized antigen. The ability of the added proteins to compete for binding of the antisera to the immobilized protein is compared to the ability of HsKif9 encoded by SEQ ID NO:2 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., HsKif9 of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a HsKif9 immunogen.

Other Assay Formats

Western blot (immunoblot) analysis is used to detect and quantify the presence of HsKif9 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind HsKif9. The anti-HsKif9 antibodies specifically bind to the HsKif9 on the solid support. These antibodies may be directly labeled or alternatively may be subsequently detected using labeled antibodies (e.g., labeled sheep anti-mouse antibodies) that specifically bind to the anti-HsKif9 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), colorimetric labels such as colloidal gold or colored glass or plastic beads (e.g., polystyrene, polypropylene, latex, etc.) or other labels that can be detected by mass spectroscopy, NMR spectroscopy, or other analytical means known in the art.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize HsKif9, or secondary antibodies that recognize anti-HsKif9.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of the Target Protein
A. Functional Assays

Assays that can be used to test for modulators of the target protein include a variety of in vitro or in vivo assays, e.g., microtubule gliding assays, binding assays such as microtubule binding assays, microtubule depolymerization assays, and ATPase assays (Kodama et al., J. Biochem. 99: 1465–1472 (1986); Stewart et al., Proc. Nat'l Acad. Sci. USA 90: 5209–5213 (1993); (Lombillo et al., J. Cell Biol. 128:107–115 (1995); (Vale et al., Cell 42:39–50 (1985)).

Modulation is tested by screening for candidate agents capable of modulating the activity of the target protein comprising the steps of combining a candidate agent with the target protein, as above, and determining an alteration in the biological activity of the target protein. Thus, in this embodiment, the candidate agent should both bind to the target protein (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

In a preferred embodiment, molecular motor activity is measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound. For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the E. coli phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect.

Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigma). Suitable surfactants include, but are not limited to, Tween, Tritons, including Triton X-100, saponins, and polyoxyethylene ethers. Generally, the antifoams, detergents, or surfactants are added at a range from about 0.01 ppm to about 10 ppm.

A preferred assay design is also provided. In one aspect, the invention provides a multi-time-point (kinetic) assay, with at least two data points being preferred. In the case of multiple measurements, the absolute rate of the protein activity can be determined.

B. Binding Assays

In a preferred embodiment, the binding of the candidate agent is determined through the use of competitive binding assays. In this embodiment, the competitor is a binding moiety known to bind to the target protein, such as an antibody, peptide, binding partner, ligand, etc. Under certain circumstances, there may be competitive binding as between the candidate agent and the binding moiety, with the binding moiety displacing the candidate agent.

Competitive screening assays may be done by combining the target protein and a drug candidate in a first sample. A second sample comprises a candidate agent, the target protein and a compound that is known to modulate the target protein. This may be performed in either the presence or absence of microtubules. The binding of the candidate agent is determined for both samples, and a change, or difference in binding between the two samples indicates the presence of an agent capable of binding to the target protein and potentially modulating its activity. That is, if the binding of the candidate agent is different in the second sample relative to the first sample, the candidate agent is capable of binding to the target protein.

In one embodiment, the candidate agent is labeled. Either the candidate agent, or the competitor, or both, is added first to the target protein for a time sufficient to allow binding. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to the target protein and thus is capable of binding to, and potentially modulating, the activity of the target protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an arnine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

D. Other Assay Components

The assays provided utilize target protein as defined herein. In one embodiment, portions of target protein are utilized; in a preferred embodiment, portions having target protein activity as described herein are used. In addition, the assays described herein may utilize either isolated target proteins or cells or animal models comprising the target proteins.

A variety of other reagents may be included in the screening assays. These include reagents like salts, neutral proteins, e.g. albumin, detergents, etc which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

VII. Applications

The methods of the invention are used to identify compounds useful in the treatment of cellular proliferation diseases. Disease states which can be treated by the methods and compositions provided herein include, but are not limited to, cancer (further discussed below), autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesotheliorna; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinorna, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinorna, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt. %. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations. The administration of the candidate agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the candidate agents may be directly applied as a solution or spray.

One of skill in the art will readily appreciate that the methods described herein also can be used for diagnostic applications. A diagnostic as used herein is a compound or method that assists in the identification and characterization of a health or disease state in humans or other animals. More specifically, antibodies which specifically bind HsKif9 may be used for the diagnosis of disorders characterized by expression of HsKif9 or in assays to monitor patients being treated with HsKif9, or agonists, antagonists, or inhibitors of HsKif9. Diagnostic assays include methods which utilize the antibody and a label to detect HsKif9 in human body fluids or in extracts of cells or tissues. The antibodies may be used with or without modification, and may be labeled by covalent or non-covalent attachment of a reporter molecules. A wide variety of reporter molecules are known in the art and may be used.

A variety of protocols for measuring HsKif9, including ELISAs, RIAs, and FACS, are known in the art and provide a basis for diagnosing altered or abnormal levels of HsKif9 expression. Normal or standard values for HsKif9 expression are established by coming body fluids or cell extracts taken from normal mammalian subjects, preferably human, with antibody to HsKif9 under conditions suitable for complex formation. The amount of standard complex formation may be quantitated by various methods, preferably by photometric means. Quantities of HsKif9 expressed in subject, control, and disease samples from biopsied tissues can be compared with the standard values. Deviation between standard and subject values establishes the parameters for diagnosing disease.

In another embodiment of the invention, the polynucleotides encoding HsKif9 may be used for diagnostic purposes. The polynucleotides which may be used include oligonucleotide sequences, complementary RNA and DNA molecules, and PNAs. The polynucleotides may be used to detect and quantitate gene expression in biopsied tissues in which HsKif9 may be correlated with disease. The diagnostic assay may be used to determine absence, presence, and excess expression of HsKif9, and to monitor regulation of HsKif9 levels during therapeutic intervention.

In one aspect, hybridization with PCR probes which are capable of detecting polynucleotide sequences, including genomic sequences encoding HsKif9 or closely related molecules may be used. The specificity of the probe, whether it's made from a highly specific region or from a less specific region, and the stringency of the hybridization or amplification (maximal, high, intermediate, or low) will determine whether the probe identifies only naturally occurring sequences encoding HsKif9, allelic variants, or related sequences.

Probes may also be used for the detection of related sequences, and should preferably have at least 50% sequence identity to any of the HsKif9 encoding sequences. The hybridization probes of the subject invention may be DNA or RNA and may be derived from the sequence of SEQ ID NO:1 or SEQ ID NO:3 or from genomic sequences including promoters, enhancers, and introns of the HsKif9 gene.

Means for producing specific hybridization probes for DNAs encoding HsKif9 include the cloning of polynucleotide sequences encoding HsKif9 or derivatives thereof into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems and the like.

In a particular aspect, the nucleotide sequences encoding HsKif9 may be useful in assays that detect the presence of associated disorders. The nucleotide sequences encoding HsKif9 may be labeled by standard methods and added to a fluid or tissue sample from a patient under conditions suitable for the formation of hybridization complexes. After a suitable incubation period, the sample is washed and the signal is quantitated and compared with a standard value. If the amount of signal is significantly altered in comparison to a control sample then the presence of altered levels of nucleotide sequences encoding HsKif9 in the sample indicates the presence of the associated disorder. Such assays may also be used to evaluate the efficacy of a particular therapeutic treatment regimen in animal studies, in clinical trials, or to monitor the treatment of an individual patient.

Additional diagnostic uses for oligonucleotides designed from the sequences encoding HsKif9 may involve the use of PCR. These oligomers may be chemically synthesized, generated enzymatically, or produced in vitro. Oligomers will preferably contain a fragment of a polynucleotide encoding HsKif9, or a fragment of a polynucleotide complementary to the polynucleotide encoding HsKif9, and will be employed under optimized conditions for identification of a specific gene or condition. Oligomers may also be employed under less stringent conditions for detection or quantitation of closely related DNA or RNA sequences.

Methods which may be used to quantitate the expression of HsKif9 include radiolabeling or biotinylating nucleotides, coamplification of a control nucleic acid, and interpolating results from standard curves. The speed of quantitation of multiple samples may be accelerated by running the assay in an ELISA format where the oligomer of interest is presented in various dilutions and a spectrophotometer or colorimetric response gives rapid quantitation.

One of skill in the art will readily appreciate that the methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for ATPase assays, microtubule gliding assays, or microtubule binding assays.

VIII. Examples

This assay is based on detection of ADP production from a target protein's microtubule stimulated ATPase. ATP production is monitored by a coupled enzyme system consisting of pyruvate kinase and lactate dehydrogenase. Under the assay conditions described below, pyruvate kianse catalyzes the conversion of ADP and phosphoenol pyruvate to pyruvate and ATP. Lactate dehydrogenase then catalyzes the oxidation-reduction reaction of pyruvate and NADH to lactate and NAD+. Thus, for each molecule of ADP produced, one molecule of NADH is consumed. The amount of NADH in the assay solution is monitored by measuring light absorbance at a wavelength of 340 nm.

The final 25 µl assay solution consists of the following: 5 µg/ml target protein, 30 µg/ml microtubules, 5 µM Taxol, 0.8 mM NADH, 1.5 mM phosphoenol pyruvate, 3.5 U/ml pyruvate kinase, 5 U/ml lactate dehydrogenase, 25 mM Pipes/KOH pH 6.8, 2 mM $MgCl_2$, 1 mM EGTA, 1 mM MDTT, 0.1 mg/ml BSA, 0.001% antifoam 289, and 1 mM ATP.

Potential candidate agents are dissolved in DMSO at a concentration of about 1 mg/ml and 0.5 µl of each chemical solution is dispensed into a single well of a clear 384 well plate. Each of the 384 wells are then filled with 20 µl of a solution consisting of all of the assay components described above except for ATP. The plate is agitated at a high frequency. To start the assay, 5 µl of a solution containing ATP is added to each well. The plate is agitated and the absorbance is read at 340 nm over various time intervals. The assay is run at room temperature.

The assay components and the performance of the assay are optimized together to match the overall read time with the rate of the target protein's ADP production. The read time should be long enough for the rate of NADH consumption to reach steady state beyond an initial lag time of several seconds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. An isolated microtubule motor protein, having microtubule stimulated ATPase activity wherein the protein comprises an amino acid sequencing having greater than 95% amino acid sequence identity to SEQ ID NO:2 as measured using BLAST sequence comparison algorithm.

2. An isolated protein of claim 1, wherein the protein specifically binds to polyclonal antibodies generated against a protein having an amino acid sequence of SEQ ID NO:2.

3. An isolated protein comprising an amino acid sequence of SEQ ID NO:2 or SEQ ID NO:4.

4. An isolated protein of claim 3, wherein the protein comprises an amino acid sequence of SEQ ID NO:2.

5. An isolated protein of claim 3, wherein the protein comprises an amino acid sequence of SEQ ID NO:4.

6. An isolated protein of claim 1, wherein the protein comprises an amino acid sequence having greater than 98% amino acid sequence identity to SEQ ID NO:2 as measured using a BLAST sequence comparison algorithm.

7. An isolated protein of claim 1, wherein the protein is tagged at its C-terminal with a myc epitope and six histidines.

8. The protein of claim 1, wherein the protein is tagged at its N-terminus with a T7 epitope.

9. The protein of claim 3, wherein the protein is tagged at its N-terminus with a T7 epitope.

10. An isolated protein of claim 3, wherein the protein is tagged at its C-terminal with a myc epitope and six histidines.

11. An isolated protein, having microtubule stimulated ATPase activity wherein the protein comprises an amino acid sequence having greater than 98% amino acid sequence identity to SEQ ID NO:4 as measured using a sequence comparison algorithm.

12. An isolated protein of claim 11, wherein the protein is tagged at its C-terminal with a myc epitope and six histidines.

13. The protein of claim 11, wherein the protein is tagged at its N-terminus with a T7 epitope.

* * * * *